United States Patent [19]

Elliott et al.

[11] Patent Number: 5,686,481
[45] Date of Patent: Nov. 11, 1997

[54] ENDOTHELIN RECEPTOR ANTAGONISTS

[75] Inventors: John Duncan Elliott, Wayne; Jack Dale Leber, Doylestown, both of Pa.

[73] Assignee: SmithKline Beecham Corporation, Philadelphia, Pa.

[21] Appl. No.: 464,613

[22] PCT Filed: Dec. 21, 1993

[86] PCT No.: PCT/US93/12435

§ 371 Date: Jun. 20, 1995

§ 102(e) Date: Jun. 20, 1995

[87] PCT Pub. No.: WO94/14434

PCT Pub. Date: Jul. 7, 1994

[51] Int. Cl.⁶ .............. A61K 31/40; A61K 31/405; C07D 209/12; C07D 209/22
[52] U.S. Cl. .............. 514/414; 514/419; 548/454; 548/492
[58] Field of Search .............. 514/414, 419; 548/454, 492

[56] References Cited

U.S. PATENT DOCUMENTS 4,822,375  4/1989  Lang et al. .
4,924,004  5/1990  Ohlendorf et al. .
5,013,732  5/1991  Bell .

FOREIGN PATENT DOCUMENTS 0 449 196 A2  10/1991  European Pat. Off. ...... C07D 209/42
0 460 679 A2  12/1991  European Pat. Off. ...... C07K 5/02
1214502  12/1967  United Kingdom .

*Primary Examiner*—Jacqueline Haley
*Attorney, Agent, or Firm*—Linda E. Hall; Stephen A. Venetianer; Edward T. Lentz

[57] ABSTRACT

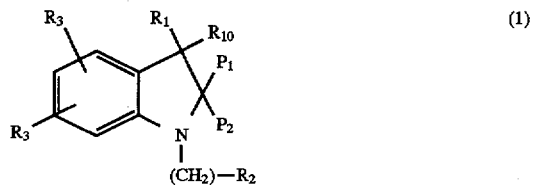

Indole derivatives of formula (1) wherein the substituents are defined herein are disclosed. The compounds are useful in methods of antagonizing endothelin receptors, treating hypertension, treating renal failure and treating cerebrovascular disease. Pharmaceutical compositions are also disclosed.

10 Claims, No Drawings

ENDOTHELIN RECEPTOR ANTAGONISTS

This is a National Stage application of PCT/US93/12435 filed Dec. 21, 1993 and published as WO 94/14434 on Jul. 7, 1994.

FIELD OF THE INVENTION

The present invention relates to novel indole derivatives, pharmaceutical compositions containing these compounds and their use as endothelin receptor antagonists.

BACKGROUND

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al. Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et. al., Am. J. Physiol. 258:408–C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplasty (Kadel et al., No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al., Lancet, 337: 697–701, 1991).

Endothelin has been associated with the induction of haemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Migraine (Edmeads, Headache, February 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int, 37: 1487–1491, 1990) and endotoxin shock and other endotoxin induced diseases (Biochem. Biophys. Res. Commun., 161: 1220–1227, 1989, Acta Physiol. Scand. 137: 317–318, 1989).

Thus, endothelin receptor antagonists would offer a unique approach toward the pharmacotherapy of hypertension, renal failure, cerebrovascular disease, myocardial ischemia, angina, heart failure, asthma, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty and prevention of restenosis.

SUMMARY OF THE INVENTION

This invention comprises indole derivatives represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure and atherosclerosis.

This invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

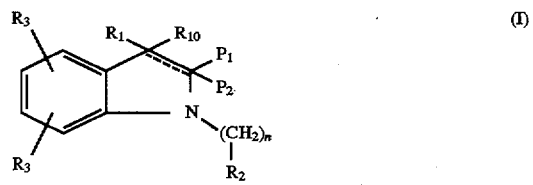

wherein:

$R_1$ is —$X(CH_2)_n Ar$ or —$X(CH_2)_n R_8$ or

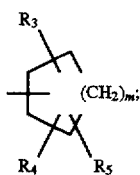
(c)

$R_2$ is hydrogen, Ar or (c);

$P_1$ is —$X(CH_2)_n R_8$;

$P_2$ is —$X(CH_2)_n R_8$, or —$XR_9 Y$;

$R_3$ and $R_5$ are independently hydrogen, $R_{11}$, OH, $C_{1-8}$alkoxy, $S(O)_q R_{11}$, $N(R_6)_2$, Br, F, I, Cl, $CF_3$, $NHCOR_6$, —$R_{11}CO_2R_7$, —$XR_9$—Y, XY or —$X(CH_2)_n R_8$ wherein the methylene groups of —$X(CH_2)_n R_8$ may be unsubstituted or substituted by one or more —$(CH_2)_n Ar$ groups;

$R_4$ is hydrogen, Ar, $R_{11}$, OH, $C_{1-5}$alkoxy, $S(O)_q R_{11}$, $N(R_6)_2$, —$X(R_{11})$, Br, F, I, Cl or $NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-5}$alkyl or $(CH_2)_n Ar$;

$R_8$ is hydrogen, $R_{11}$, $CO_2R_7$, $CO_2C(R_7)_2O(CO)XR_7$, —$N(R_7)SO_2R_7$, $PO_3(R_7)_2$; $SO_2NR_7R_{11}$, $CONR_7SO_2R_{11}$, $SO_3R_7SO_2R_7$, $SO_3R_7$, $SO_2R_7$, $P(O)(OR_7)R_7$, CN, —$C(O)N(R_6)_2$, tetrazole or $OR_6$;

$R_9$ is $C_{1-10}$alkyl, $C_{2-10}$alkenyl or phenyl all of which may be unsubstituted or substituted by one or more OH, $N(R_6)_2$, COOH, halogen or $XC_{1-5}$alkyl;

$R_{10}$ is $R_3$ or $R_4$;

$R_{11}$ is $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

X is $(CH_2)_n$, O, $NR_6$ or $S(O)_q$;

Y is $CH_3$ or —$X(CH_2)_n Ar$;

Ar is:

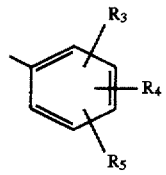
(a)

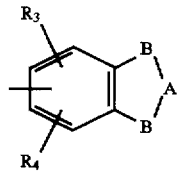
(b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or $(C(R_6)_2)_m$;

B is —$CH_2$— or , —O—;

q is zero, one or two;

n is an integer from 0 to six;

m is 1, 2 or 3;

and the dotted line indicates the optional presence of a double bond; or a pharmaceutically acceptable salt thereof; provided that when the optional double bond is present there is no $P_1$ or $R_{10}$ and further provided that X is not oxygen in the definition of $R_1$.

Also included in the invention are pharmaceutically acceptable salt complexes.

All alkyl, alkenyl, alkynyl and alkoxy groups may be straight or branched. The term "halogen" is used to mean iodo, fluoro, chloro or bromo. Alkyl groups may be substituted by one or more halogens up to perhalogenation. The substituents listed for $R_9$ and $R_{11}$ may be monovalent or divalent depending on their position in order to conform with the general laws of chemistry.

The compounds of the present invention may contain one or more asymmetric carbon atoms and may exist in racemic and optically active form. All of these compounds and diastereoisomers are contemplated to be within the scope of the present invention.

Preferred compounds are those wherein $R_1$ is $X(CH_2)_n Ar$, (Ar is (a) or (b)), dihydrobenzofuranyl, benzodioxanyl, cyclohexyl, or $C_{1-4}$alkyl; $R_2$ is (a), (b), $C_{1-4}$alkyl, indolyl or hydrogen; $R_3$ and $R_5$ are independently hydrogen, OH, $C_{1-5}$alkoxy, halogen, —$OC_{1-4}$alkyl phenyl, $R_{11}CO_2R_7$, $C_{1-4}$alkyl, $N(R_6)_2$, $NH(CO)CH_3$, —$X(CH_2)_n R_8$, —$XR_9$ pyridyl, phenyl or $S(O)_p C_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_p C_{1-5}$alkyl; $P_1$ and $P_2$ are independently hydrogen, $CO_2H$ or tetrazole; Ar is (a), (b), phenyl, or pyridyl; and X is $(CH_2)_n$ or oxygen.

More preferred are compounds wherein $R_3$ is hydrogen or —$X(CH_2)_n R_8$, $R_{11}CO_2R_7$; $R_4$ and $R_5$ are independently hydrogen, OH, $C_{1-5}$alkoxy, $SC_{1-5}$alkyl, F, Br, $C_{1-3}$alkyl or $NH_2$.

Most preferred are compounds wherein $R_1$ is (b) and $R_2$ is (a) or (b); A is $CH_2$, B is —O—; there is an optional double bond; $R_3$ is hydrogen, $X(CH_2)_q COOH$ or $CH=CHCO_2H$, $R_4$ is hydrogen, substituted phenyl, or $C_{1-2}$alkoxy; and $R_5$, $R_{10}$ and $P_2$ are hydrogen.

Especially preferred are the following compounds:

1-(3,4-Methylenedioxybenzyl)-3-(4-methoxyphenyl) indole-2-carboxylic acid;

1-(2-Chloro-4,5-methylenedioxybenzyl)-3-(4-methoxyphenyl)indole-2-carboxylic acid;

3-(3,4-Methylenedioxyphenyl)-1-(4-methoxybenzyl) indole-2-carboxylic acid;

3-(2-Carboxymethoxy-4-methoxyphenyl)-1-(2-chloro-4,5-methylenedioxybenzyl)indole-2-carboxylic acid;

5-Benzyloxy-1-(2-carboxymethoxy-4-methoxybenzyl)-3-(3,4-methylenedioxyphenyl)indole-2-carboxylic acid;

1-(2-Carboxymethoxy-4-methoxybenzyl)-5-hydroxy-3-(3,4-methylenedioxyphenyl)indole-2-carboxylic acid;

1-(2-Carboxymethoxy-4-methoxybenzyl)-3-(3,4-methylenedioxyphenyl)-5-(prop-1-yloxy)indole-2-carboxylic acid;

5-Carboxymethoxy-1-(2-carboxymethoxy-4-methoxybenzyl)-3-(3,4-methylenedioxyphenyl)indole-2-carboxylic acid;

1-(2-Carboxymethoxy-4-methoxybenzyl)-3-(3,4-methylenedioxyphenyl)indole-2-carboxylic acid;

4-[1-[2-Carboxy-3-(3,4-methylenedioxyphenyl)indolyl]]-4-(4-methoxyphenyl)butyric acid.

The present invention provides compounds of Formula (1) above,

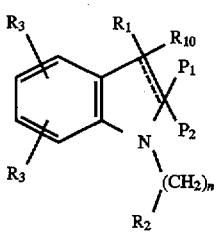

which can be prepared by a process which comprises:

a) for compounds in which the optional double bond is present and there is no $R_{10}$ or $P_1$, reacting a compound of Formula (2),

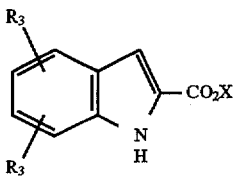

wherein X is $C_{1-5}$ alkyl, with bromine in a suitable solvent such as dimethylformamide to provide a bromoindole of Formula (3).

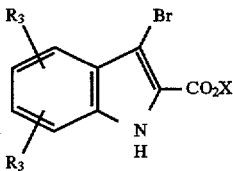

Coupling of Compound (3) with a boronic acid of formula (4):

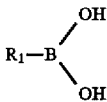

in the presence of a palladium (O) catalyst, such as tetrakis (triphenylphosphine)palladium (O), in a solvent such as toluene/methanol in the presence of a base such as aqueous sodium carbonate, at approximately 100° C., provides an indole of Formula (5).

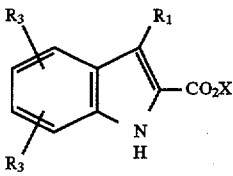

Aryl boronic acids of Formula (4) may be prepared by transmetallation of aryl halides of Formula (6):

wherein Hal is Cl, Br or I, with an alkyllithium, such as n-butyllithium in a solvent such as dry tetrahydrofuran at low temperature (−40°—78° C.) followed by quenching with a trialkylborate, such as tri-isopropylborate, then treatment with an acid such as aqueous hydrochloric.

For compounds in which n is not O, alkylation of an indole of Formula (5) with an halide of Formula (7):

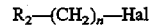

in a suitable solvent such as dimethylformamide or hexamethylphosphoramide in the presence of a suitable base such as sodium hydride affords compounds of Formula (8), n is not zero.

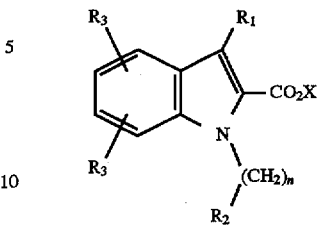

Saponification of esters of Formula (8) with aqueous sodium hydroxide in a solvent such as ethanol or isopropanol at reflux affords compounds of Formula (9), n is not zero.

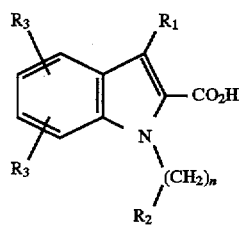

Alternatively, compounds of Formula (5) may be obtained by coupling of compound of type (3) with an aryl stannane derivative of Formula (10):

in the presence of a palladium (O) catalyst such as tetrakis (triphenylphosphine)palladium (O) in a solvent such as dioxan or dimethylformamide at approximately 100° C. in the presence of anhydrous lithium chloride. Aryl stannanes of Formula (10) may be prepared by transmetallation of aryl halides of Formula (6) with an alkyllithium, such as n-butyllithium, in a solvent such as tetrahydrofuran at low temperature (−40°—78° C.) followed by quenching with a trialkylchlorostannane of Formula (11).

b) As an alternative compounds of Formula (3) may be alkylated with an halide of Formula (7),n#0 in a suitable solvent such as dimethylformamide or hexamethylphosphoramide in the presence of a suitable base such as sodium hydride to afford compounds of Formula (12), n is not 0.

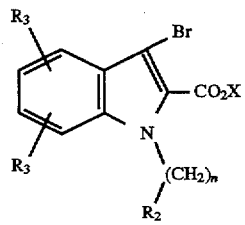

Coupling of Compound (12) with a boronic acid of formula (4) in the presence of a palladium (O) catalyst, such as tetrakis(triphenylphosphine)palladium (O), in a solvent such as toluene/methanol in the presence of a base such as aqueous sodium carbonate, at approximately 100° C., provides compounds of Formula (8) n is not zero.

As an alternative compounds of Formula (8) n is not zero, may be obtained by coupling of compound (12) with an aryl stannane derivative of Formula (10) in the presence of a palladium (O) catalyst such as tetrakis(triphenylphosphine)

palladium (O) in a solvent such as dioxan or dimethylformamide at approximately 100° C. in the presence of anhydrous lithium chloride.

c) As a further alternative, compounds of Formula (5) may be prepared by a process which comprises:

alkylation of an ester of acetoacetic acid (13)

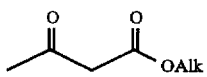
(13)

with a halide of Formula (14)

R₁—CH₂Hal  (14)

in a suitable solvent such as acetonitrile and a base such as 1,8 diazabicyclo[5.4.0]undec-7-ene to afford compounds of Formula (15). Alternatively tetrahydrofuran may be used as the solvent and sodium hydride as the base for the alkylation.

(15)

Treatment of a compound of type (15) with an aryl diazonium chloride of Formula (16)

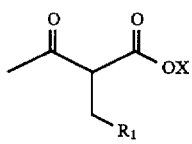
(16)

in a suitable solvent such as ethyl acetate in the presence of a base such as aqueous sodium hydroxide solution affords, by Japp-Klingemann rearrangement, hydrazones of Formula (17).

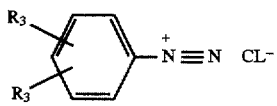
(17)

Treatment of hydrazones of type (17) with a suitable acid such as gaseous hydrogen chloride in a solvent such as ethanol followed by reflux for a period from 0.5 to 12 hours affords indoles of Formula (5).

d) Compounds of type (1) where n is 0–6 may be prepared by a process which comprises:

treatment of a compound of Formula (18)

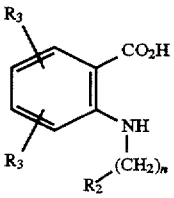
(18)

with aqueous formaldehyde solution at reflux affords a product of Formula (19).

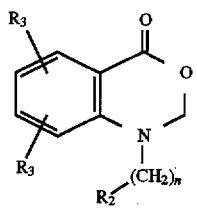
(19)

Treatment of compounds of type (19) with aqueous potassium cyanide at approximately 40°–50° C., affords nitriles of Formula (20).

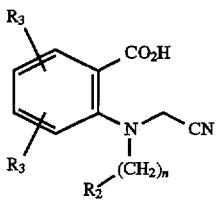
(20)

Hydrolysis of a nitrile of type (20) with aqueous sodium hydroxide at reflux followed by acidification with an acid such as hydrochloric affords diacids of Formula (21).

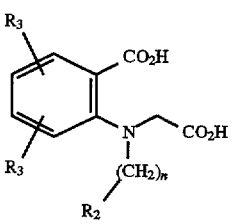
(21)

Diesterification of compounds of type (21) is achieved by treatment with a suitable base such as 1,8 diazabicyclo [5.4.0]undec-7-ene in a solvent such as acetonitrile or dimethylformamide followed by addition of iodomethane to afford compounds of Formula (22).

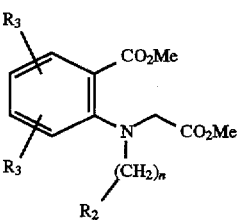
(22)

Dieckmann cyclization of diesters of type (22) using a base such as sodium methoxide and methanol as solvent at reflux affords products of Formula (23).

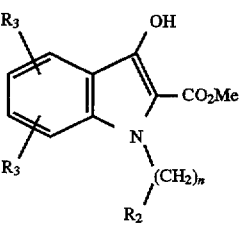
(23)

Treatment of compounds of type (23) with trifluoromethanesulfonic anhydride in pyridine as solvent affords triflates of Formula (24)

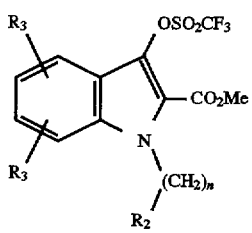

(24)

Compounds of Formula (8), X=Me, may be obtained by coupling of compound (24) with an aryl stannane derivative of Formula (10) in the presence of a palladium (O) catalyst such as tetrakis(triphenylphosphine)palladium (O) in a solvent such as dioxan or dimethylformamide at approximately 100° C. in the presence of anhydrous lithium chloride.

As an alternative compounds of Formula (8), X=Me, can be prepared by coupling of compound (24) with a boronic acid of formula (4) in the presence of a palladium (O) catalyst, such as tetrakis(triphenylphosphine)palladium (O), in a solvent such as toluene/methanol in the presence of a base such as aqueous sodium carbonate, at approximately 100° C.

Saponification of compounds of Formula (8), X is Me, to provides indole-2-carboxylic acids of Formula (9) can be achieved by treatment with aqueous sodium hydroxide in a solvent such as ethanol or isopropanol at reflux.

With appropriate manipulation and protection of any chemical functionalities, synthesis of the remaining compounds of the Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sublingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg, and preferably from 1 mg to 100 mg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) Membrane Preparation

Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000×g for 10 minutes at 4° C. The supernatant was removed and centrifuged at 40,000×g for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.

Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteric artery bed. The homogenate was strained through cheesecloth and centrifuged at 2,000×g for 10 min. at 4° C. The supernatant was removed and centrifuged at 40,000×g for 30 min. at 4° C. The resulting pellet was resuspended as explained above for cerebellum and kidney cortex. Approximately 10 mg of membrane protein was used for each tube in binding experiments.

B) [$^{125}$I]ET-1 Binding Protocol

[$^{125}$I]ET-1 binding to membranes from rat cerebellum (2-5 mg protein/assay tube) or kidney cortex (3-8 mg protein/assay tube) were measured after 60 minutes incubation at 30° C. in 50 mM Tris HCl, 10 mM MgCl$_2$, 0.05% BSA, pH 7.5 buffer in a total volume of 100 ml. Membrane protein was added to tubes containing either buffer or indicated concentration of compounds. [$^{125}$I]ET-1 (2200 Ci/mmol) was diluted in the same buffer containing BSA to give a final concentration of 0.2-0.5 nM ET-1. Total and nonspecific binding were measured in the absence and presence of 100 nM unlabelled ET-1. After the incubation, the reactions were stopped with 3.0 ml cold buffer containing 50 mM Tris and 10 mM MgCl$_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. IC$_{50}$'s for the compounds of this invention range from 0.1 nm to 50 µm.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; KH$_2$PO$_4$, 1.2; MgSO$_4$, 1.2; CaCl$_2$, 2.5; NaHCO$_3$, 25.0; and dextrose, 11.0. Tissue bath solutions are maintained at 37° C. and aerated continuously with 95% O$_2$/5% CO$_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean±S.E.M. Dissociation constants (K$_b$) of competitive antagonists were determined by the standard method of Arunlakshana and Schild. The potency range for compounds of this invention range from 0.1 nM to 50 µm.

The following examples are illustrative and are not limiting of the compounds of this invention.

EXAMPLE 1

1-(3,4-Methylenedioxybenzyl)-3-(4-methoxyphenyl)indole-2-carboxylic acid a) Ethyl 2-(4-methoxybenzyl)-3-oxybutyrate. To a stirred solution of ethyl acetoacetate (4.17 g, 31.9 mmol) and 4-methoxybenzyl chloride (5.0 g, 31.9 mmol) in CH$_3$CN (25 mL) under an argon atmosphere was added 1,8-diazabicyclo[5.4.0]undec-7-ene (4.86 g, 31.9 mmol). After 3 h at room temperature, the mixture was partitioned between 3N HCl (100 mL) and EtOAc (200 mL). The organic extract was washed successively with H$_2$O, aqueous NaHCO$_3$, H$_2$O and saturated aqueous NaCl and dried (Na$_2$SO$_4$). The solvent was removed in vacuo to afford the title compound as an oil (6.65 g, 84%) which was used in the next step without further purification.

b) Ethyl 3-(4-methoxyphenyl)indole-2-carboxylate. To a solution of ethyl 2-(4-methoxybenzyl)-3-oxobutyrate (1.0 g, 4 mmol) in EtOAc (6 mL) stirred at ice bath temperature under an argon atmosphere was added a solution of NaOH (0.48 g, 12 mmol) in H$_2$O (2 mL). This was immediately followed by the addition of an aqueous solution of benzenediazonium chloride (4.2 mmol) [prepared from aniline, (0.39 g, 4.2 mmol) in 6N HCl (0.5 mL) and NaNO$_2$ (0.29 g, 4.2 mmol)]. After 10 min the mixture was partitioned between EtOAc (50 mL) and H$_2$O (25 mL). The aqueous layer was washed with EtOAc (15 mL). The combined organic extracts were washed with saturated aqueous NaCl solution, dried (Na$_2$SO$_4$) and the solvent was removed in vacuo. The residue was dissolved in EtOH (10 mL) and the solution was saturated with HCl gas. This was refluxed for 1 h then cooled to room temperature and partitioned EtOAc (50 mL) and saturated aqueous NaHCO$_3$ solution (50 mL). The aqueous layer was washed with EtOAc (15 mL). The combined organic extract was washed with H$_2$O then saturated aqueous NaCl solution, dried (Na$_2$SO$_4$) and the solvent was removed in vacuo. Chromatography (silica gel, gradient elution from 25% Et$_2$O/hexanes to 45% Et$_2$O/hexanes) followed by crystallization from EtOAc/hexanes to afford the title compound (0.32 g, 27%); m.p. 109°-111° C.

c) Ethyl 1-(3,4-methylenedioxybenzyl)-3-(4-methoxyphenyl)indole-2-carboxylate. To a solution of ethyl 3-(4-methoxyphenyl)indole-2-carboxylate (110 mg, 0.37 mmol) in HMPA (2 mL) stirred at ice bath temperature under an argon atmosphere was added NaH (14 mg of 80% oil dispersion, 0.46 mmol, oil removed by pentane wash). After 15 min a solution of piperonyl chloride (128 mg, 0.75 mmol) in HMPA (0.5 mL) was added and the ice bath removed. The reaction mixture was stirred 7 h at room temperature then partitioned between 3N HCl (25 mL) and EtOAc (50 mL). The organic extract was washed successively with H$_2$O, aqueous NaHCO$_3$, H$_2$O and saturated aqueous NaCl and dried (Na$_2$SO$_4$). The solvent was removed in vacuo. The residue was purified by chromatography (silica gel, gradient elution from 25% Et$_2$O/hexanes to 45% Et$_2$O/hexanes) to afford the title compound (105 mg, 66%)

d) 1-(3,4-Methylenedioxybenzyl)-3-(4-methoxyphenyl)indole-2-carboxylic acid. A solution of ethyl 1-(3,4-methylenedioxybenzyl)-3-(4-methoxyphenyl)indole-2-carboxylate (35 mg, 0.08 mmol) in EtOH (10 mL) with aqueous 1N NaOH (0.45 mL) was stirred under an argon atmosphere at room temperature for 17 h then refluxed for 3 h. The reaction mixture was cooled to room temperature then poured into H$_2$O (20 mL) and the solvent volume was reduced to ca. 20 mL under reduced pressure. The aqueous solution was extracted with Et$_2$O (15 mL) and the Et$_2$O extract discarded. The aqueous layer was acidified with 6N HCl and the product extracted into EtOAc. The organic extract was washed with H$_2$O then saturated aqueous NaCl, dried (Na$_2$SO$_4$) and the solvent removed in vacuo. Crystallization from EtOAc/hexanes afforded the title compound (21 mg, 66%); m.p. 205°-206° C.

EXAMPLE 2

1-(2-Chloro-4,5-methylenedioxybenzyl)-3-(4-methoxyphenyl)indole-2-carboxylic acid a) 1-(2-Chloro-4,5-methylenedioxybenzyl)-3-(4-methoxyphenyl)indole-2-carboxylic acid. To a solution of ethyl 3-(4-methoxyphenyl)indole-2-carboxylate (365 mg, 1.24 mmol) in HMPA (3 mL) stirred at ice bath temperature under an argon atmosphere was added NaH (46.5 mg of 80% oil dispersion, 1.55 mmol, oil removed by pentane wash). After 15 min at ice bath temperature, a solution of 6-chloropiperonyl chloride (753 mg, 1.86 mmol) in HMPA (1 mL) was added and the ice bath removed. The reaction mixture was stirred 18 h at room temperature then partitioned between 3N HCl (25 mL) and EtOAc (50 mL). The organic extract was washed successively with $H_2O$, saturated aqueous NaCl and dried ($Na_2SO_4$). The solvent was removed in vacuo and the residue (a mixture of acid and ethyl ester) was dissolved in EtOH (30 mL) and aqueous 2N NaOH (2.5 mL) was added. This was then stirred under an argon atmosphere at reflux temperature for 3 h then cooled to room temperature and poured into $H_2O$ (50 mL). The solvent volume was reduced to ca. 45 mL under reduced pressure. The aqueous solution then extracted with $Et_2O$ (20 mL) and the $Et_2O$ extract discarded. The aqueous layer was acidified with 6N HCl and the product extracted into EtOAc. The organic extract was washed with $H_2O$ then saturated aqueous NaCl and dried ($Na_2SO_4$). Removal of the solvent in vacuo yielded a yellow gum (497 mg). A portion (70 mg) was purified by reverse phase chromatography ($CH_3CN$/$H_2O$=55/45) followed by crystallization from EtOAc/hexanes to afford the title compound (50 mg); m.p. 204°–205° C.

MS: 453 [$(M+NH_4)^+$].

Anal. calc. for $C_{24}H_{18}ClNO_5 \cdot \frac{1}{4} H_2O$: C, 65.46; H, 4.23; N, 3.18. Found C, 65.38; H, 4.00; N, 2.96.

EXAMPLE 3

3-(3,4-Methylenedioxyphenyl)-1-(4-methoxybenzyl)indole-2-carboxylic acid a) Ethyl 3-bromoindole-2-carboxylate. To a solution of ethyl indole-2-carboxylate (25.0 g, 132 mmol) in DMF (50 mL), stirred at room temperature under an argon atmosphere, was added dropwise a solution of $Br_2$ (23.3 g, 145 mmol) in DMF (80 mL). Upon completion of the addition, the reaction mixture was stirred an additional 5 min then poured into ice water. The resulting solid was collected by filtration then crystallized from EtOAc/hexanes to afford the title compound (29.9 g, 85%); m.p. 149°–150° C.

b) Ethyl 3-bromo-1-(4-methoxybenzyl)indole-2-carboxylate. To a solution of ethyl 3-bromoindole-2-carboxylate (2.0 g, 7.46 mmol) and 4-methoxybenzyl chloride (7.46 mmol) in HMPA (5 mL) was added a slurry of NaH (240 mg of 80% oil dispersion, oil removed by pentane washing, 8.0 mmol) in HMPA (1 mL). After 30 min at room temperature the reaction mixture was partitioned between 3N HCl (100 mL) and EtOAc (150 mL). The organic extract was washed successively with $H_2O$, aqueous $NaHCO_3$, $H_2O$, saturated aqueous NaCl and dried ($Na_2SO_4$). The solvent was removed in vacuo to afford the title compound (2.55 g, 88%) which was used in the next step without further purification.

c) 3,4-(Methylenedioxy)phenyltributyltin. To a solution of 4-bromo-1,2-(methylenedioxy)benzene (5.0 g, 24.9 mmol) in THF (20 mL) at −78° C. under an argon atmosphere was added butyllithium (11.4 mL of a 2.4M solution in hexanes, 27.4 mmol). The mixture was warmed to 0° C. over a 10 min period then treated with tributyltin chloride (6.8 mL, 25 mmol). After 1 h the mixture was partitioned between $Et_2O$ and $H_2O$. The organic extract was washed with brine, dried ($Na_2SO_4$) and the solvent removed in vacuo. The resulting oil was purified by flash column chromatography (silica gel, with hexanes as eluent) to afford the title compound (3.64 g, 35%).

d) Ethyl 1-(4-methoxybenzyl)-3-(3,4-methylenedioxyphenyl)indole-2-carboxylate. An anhydrous solution of ethyl 3-bromo-1-(4-methoxybenzyl)indole-2-carboxylate (388 mg, 1.0 mmol), LiCl (56 mg, 1.3 mmol), 3,4-(methylenedioxy)phenyltributyltin (1.24 g, 3.0 mmol) and tetrakis(triphenylphosphine)palladium(O) (116 mg, 0.10 mmol) in DMF (5 mL) was stirred under an atmosphere of argon at 110° C. for 18 h. The reaction mixture was cooled to room temperature then partitioned between 3N HCl (25 mL) and EtOAc (75 mL). The organic extract was washed successively with $H_2O$, aqueous $NaHCO_3$, $H_2O$ and saturated aqueous NaCl and dried ($Na_2SO_4$). The solvent was removed in vacuo to yield a dark oil (1.4 g). Purification by chromatography (silica gel, eluting with 35% $Et_2O$/hexanes) followed by crystallization from $Et_2O$/hexanes afforded the title compound (270 mg, 65%).

e) 3-(3,4-Methylenedioxyphenyl)-1-(4-methoxybenzyl)indole-2-carboxylic acid. A solution of ethyl 1-(4-methoxybenzyl)-3-(3,4-methylenedioxyphenyl)indole-2-carboxylate (110 mg, 0.25 mmol) in EtOH (10 mL) and 1N aqueous NaOH solution (2.5 mL) was refluxed for 3 h. The reaction mixture was cooled to room temperature then poured into $H_2O$ (25 mL). The solvent volume was reduced to ca. 25 mL under reduced pressure. The aqueous solution then extracted with $Et_2O$ (20 mL) and the $Et_2O$ layer discarded. The aqueous layer was acidified with 6N HCl and the product extracted into EtOAc. The organic extract was washed with $H_2O$ then saturated aqueous NaCl and dried ($Na_2SO_4$). Removal of the solvent in vacuo yielded a white solid (91 mg). Crystallization from EtOAc/hexanes afforded the title compound (74 mg, 67%); m.p. 155°–157° C.

MS: 419.3 [$(M+NH_4)^+$].

Anal. Calc. for $C_{24}H_{19}NO_5 \cdot \frac{1}{4} H_2O$: C, 71.01; H, 4.84; N, 3.45. Found C, 71.24; H, 4.83; N, 3.28.

EXAMPLE 4

3-(2-Carboxymethoxy-4-methoxyphenyl)-1-(2-chloro-4,5-methylenedioxybenzyl)indole-2-carboxylic acid a) 2-Carboethoxymethoxy-4-methoxybenzaldehyde. To a solution of 2-hydroxy-4-methoxybenzaldehyde (1.315 g, 8.64 mmol) in dry DMF (5 mL) stirred at ice bath temperature under an argon atmosphere was added a slurry of NaH (300 mg of 80% oil dispersion, oil removed by pentane wash, 10 mmol) in dry DMF (2 mL). After 15 min, ethyl bromoacetate (2.84 g, 17 mmol) was added and the ice bath removed and stirring continued for an additional 30 min at room temperature. The reaction mixture was partitioned between 3N HCl (100 mL) and EtOAc (150 mL). The organic extract was washed successively with $H_2O$, aqueous $NaHCO_3$, $H_2O$, saturated aqueous NaCl and dried ($Na_2SO_4$). The solvent was removed in vacuo to yield an oil (2.55 g) which was crystallized from $Et_2O$/hexanes to afford the title compound (1.77 g, 86%); m.p. 61°–62° C.

b) Cis and trans methyl 2-aceyl-3-(2-carboethoxymethoxy-4-methoxyphenyl)acrylate. A solution consisting of 2-carboethoxymethoxy-4-methoxybenzaldehyde (17.58 g, 73.86 mmol), methyl acetoacetate (12 mL, 111 mmol), acetic acid (1.6 mL) and piperidine (0.5 mL) was refluxed in benzene for 1 h with azeotropic removal of $H_2O$. The solution was cooled and all volatiles were removed in vacuo to afford the title compound (20.46 g) as an oil which was used without further purification.

c) Methyl 2-(2-carboethoxymethoxy-4-methoxyphenyl)-3-oxobutyrate. To a solution of cis and trans methyl 2-acetyl-3-(2-carboethoxymethoxy-4-methoxyphenyl) acrylate (6.25 g, 18.6 mmol) in pyridine (25 mL) stirred at ice bath temperature under an argon atmosphere was added dropwise a slurry of NaBH4 (704 mg, 18.6 mmol) in pyridine (10 mL). After 30 min the reaction was quenched by the cautious addition of EtOAc (200 mL) and 3N HCl (200 mL). The layers were separated and the aqueous solution was washed with EtOAc. The combined organic extract was washed successively with $H_2O$, aqueous $NaHCO_3$, $H_2O$, saturated aqueous NaCl and dried ($Na_2SO_4$) and the solvent was removed in vacuo. Chromatography (silica gel eluting with 25% $Et_2O$/hexanes followed by crystallization from EtOAc/hexanes afforded the title compound (4.66 g, 74%); m.p. 60°–61° C.

d) Methyl 3-(2-carboethoxymethoxy-4-methoxyphenyl)indole-2-carboxylate. The title compound was prepared from methyl 2-(2-carboethoxymethoxy-4-methoxyphenyl)-3-oxobutyrate (2.22 g, 6.62 mmol) and phenyldiazonium chloride (0.93 g, 6.62 mmol) using methods previously described in example 1b (yield=507 mg, 25%).

e) 3-(2-Carboxymethoxy-4-methoxyphenyl)-1-(2-chloro-4,5-methylenedioxybenzyl)indole-2-carboxylic acid. The title compound was prepared by alkylation of methyl 3-(2-carboethoxymethoxy-4-methoxyphenyl)indole-2-carboxylate (100 mg, 0.27 mmol) with 6-chloropiperonyl chloride (55 mg, 0.27 mmol) followed by saponification using methods previously described in example 2a then crystallized from EtOAc as the bis(dicyclohexylamine) salt (97 mg, 41%); m.p. 154°–156° C.

MS: 510.2 [(M+H)$^+$].

Anal. calc. for $C_{26}H_{20}ClNO_8 \cdot C_{24}H_{46}N_2 \cdot \frac{1}{2} H_2O$: C, 68.12; H, 7.66; N, 4.77. Found C, 68.07; H, 7.60; N, 4.75.

EXAMPLE 5

5-Benzyloxy-1-(2-carboxymethoxy-4-methoxybenzyl)-3-(3,4-methylenedioxyphenyl)indole-2-carboxylic acid a) 3,4-Methylenedioxyphenylboric acid. To a solution of 4-bromo-1,2-(methylenedioxy)benzene (10.05 g, 50 mmol) in dry THF (40 mL) stirred under an argon atmosphere at −78° C. was added over a 3 min period BuLi (20 mL of a 2.5M solution in hexanes, 50 mmol). After 15 min at −78° C. this solution was added via cannula to a −78° C. solution of triisopropyl borate (57 mL, 250 mmol) in THF (50 mL). The cooling bath was removed and stirring continued for 40 min. The reaction mixture was partitioned between 3N HCl (200 mL) and EtOAc (250 mL). The organic extract was washed successively with $H_2O$, aqueous $NaHCO_3$, $H_2O$ and saturated aqueous NaCl and dried ($Na_2SO_4$). The solvent was removed in vacuo and the resulting solid crystallized from EtOAc/hexanes to afford the title compound (5.06 g, 61%); m.p. 247°–252° C.

b) Ethyl 5-benzyloxy-3-bromoindole-2-carboxylate. The title compound was prepared from ethyl 5-benzyloxyindole-2-carboxylate (7.80 g, 26,4 mmol) by the method previously described in example 3a (5.95 g, 60%); m.p. 147°–148° C.

c) Ethyl 5-benzyloxy-3-(3,4-methylenedioxyohenyl)indole-2-carboxylate. To a solution of ethyl 5-benzyloxy-3-bromoindole-2-carboxylate (2.39 g, 6.39 mmol) and tetrakis (triphenylphosphine)-palladium(O) (250 mg, 0.22 mmol) in toluene (32 mL) was added 2M aqueous solution of $Na_2CO_3$ (6.4 mL) and a solution of 3,4-(methylenedioxy)phenylboric acid (1.41 g, 8.5 mmol) in $CH_3OH$ (16 mL). This mixture was stirred at 90° C. under an argon atmosphere for 1 h then partitioned between 3N HCl (100 mL) and EtOAc (250 mL). The organic extract was washed successively with $H_2O$, aqueous $NaHCO_3$, $H_2O$ and saturated aqueous NaCl and dried ($Na_2SO_4$). The solvent was removed in vacuo and the resulting solid crystallized from EtOH to afford the title compound (2.38 g, 90%); m.p. 135°–136° C.

d) 2-Carboethoxymethoxy-4-methoxybenzyl alcohol. To a solution of 2-carboethoxymethoxy-4-methoxybenzaldehyde (15.50 g, 65.1 mmol) in EtOH (100 mL) and DMF (25 mL) stirred at ice bath temperature under an argon atmosphere was added portionwise $NaBH_4$ (4.93 g, 130 mmol). The ice bath was removed and stirring continued for 15 min. The reaction was quenched by the cautious addition of EtOAc (200 mL) and 3N HCl (200 mL). The layers were separated and the organic extract was washed successively with $H_2O$, aqueous $NaHCO_3$, $H_2O$, saturated aqueous NaCl and dried ($Na_2SO_4$). The solvent was removed in vacuo to afford the title compound (13.6 g, 87%) and was used without further purification.

e) 2-Carboethoxymethoxy-4-methoxybenzyl chloride. To a solution of 2-carboethoxymethoxy-4-methoxybenzyl alcohol (1.30 g, 5.4 mmol) in $Et_2O$ (50 mL) stirred at ice bath temperature under an argon atmosphere was added concentrated HCl (1.4 mL). After 15 min EtOAc (50 mL) was added and the aqueous layer removed. The organic extract was washed successively with $H_2O$, aqueous $NaHCO_3$, $H_2O$, saturated aqueous NaCl and dried ($Na_2SO_4$). The solvent was removed in vacuo to afford the title compound (1.25 g, 90%) as a white solid.

f) 5-Benzyloxy-1-(2-carboxymethoxy-4-methoxybenzyl)-3-(3,4-methylenedioxyohenyl)indole-2-carboxylic acid. The title compound was prepared by alkylation of ethyl 5-benzyloxy-3-(3,4-methylenedioxyphenyl)indole-2-carboxylate with 2-carboethoxymethoxy-4-methoxybenzyl chloride followed by saponification using methods previously described in examples 1c and 1d; m.p. 182°–190° C.

MS: 580.0 [(M−H)$^−$].

Anal. calc. for $C_{32}H_{27}NO_9 \cdot \frac{1}{4} H_2O$: C, 66.95; H, 4.83; N, 2.44. Found C, 66.90; H, 4.79; N, 2.27.

EXAMPLE 6

1-(2-Carboxymethoxy-4-methoxybenzyl)-5-hydroxy-3-(3,4-methylenedioxyphenyl)indole-2-carboxylic acid a) 1-(2-Carboxymethoxy-4-methoxybenzyl)-5-hydroxy-3-(3,4-methylenedioxyphenyl)indole-2-carboxylic acid. To a solution of 5-benzyloxy-1-(2-carboxymethoxy-4-methoxybenzyl)-3-(3,4-methylenedioxyphenyl)indole-2-carboxylic acid (120 mg, 0.21 mmol) in EtOH (30 mL) was added 10% palladium on activated carbon (12 mg). the resulting suspension was shaken in a Parr pressure reaction apparatus under 50 psi $H_2$ for 3 h, then the reaction mixture was filtered through a pad of celite. The filtrate was concentrated under reduced pressure and the residue crystallized from EtOAc/hexanes to afford the title compound (79 mg, 77%); m.p. 184°–186° C.

MS: 514.0 [(M+Na)$^+$].

EXAMPLE 7

1-(2-Carboxymethoxy-4-methoxybenzyl)-3-(3,4-methlenedioxyphenyl)-5-(prop-1-yloxy)indole-2-carboxylic acid a) Ethyl 1-(2-carboethoxymethoxy-4-methoxybenzyl)-5-hydroxy-3-(3,4-methlenedioxyphenyl)indole-2-carboxylate.

The title compound was prepared from ethyl 5-benzyloxy-1-(2-carboethoxymethoxy-4-methoxybenzyl)-3-(3,4-methylenedioxyphenyl)indole-2-carboxylate (460 mg, 0.735 mmol) by the method given in example 6; m.p. 128°–130° C.

b) Ethyl 1-(2-Carboethoxymethoxy-4-methoxybenzyl)-3-(3,4-methlenedioxyphenyl)-5-(prop-1-yloxy)indole-2-carboxylate. To a solution of ethyl 1-(2-carboethoxymethoxy-4-methoxybenzyl)-5-hydroxy-3-(3,4-methylenedioxyphenyl)indole-2-carboxylate (175 mg, 0.30 mmol) in DMF stirred at ice bath temperature under an argon atmosphere was added a slurry of NaH (11 mg of 80% oil dispersion, 0.36 mmol, oil removed by pentane wash) in DMF (1 mL). After 15 min at ice bath temperature, 1-iodopropane (0.255 g, 1.5 mmol) was added and the ice bath was removed. The reaction mixture was stirred an additional 30 min at room temperature then partitioned between 3N HCl (25 mL) and EtOAc (75 mL). The organic extract was washed successively with $H_2O$, aqueous $NaHCO_3$, $H_2O$ and saturated aqueous NaCl and dried ($Na_2SO_4$). The solvent was removed in vacuo and the resulting solid crystallized from EtOH to afford the title compound (83 mg 47%); m.p. 89°–91° C.

c) 1-(2-Carboxymethoxy-4-methoxybenzyl)-3-(3,4-methylenedioxyphenyl)-5-(prop-1-yloxy)indole-2-carboxylic acid. The title compound was prepared from ethyl 1-(2-carboethoxymethoxy-4-methoxybenzyl)-3-(3,4-methylenedioxyphenyl)-5-(prop-1-yloxy)indole-2-carboxylate (50 mg, 0.085 mmol) by the method given in example 3d (33 mg, 73%); m.p. 190°–191° C.

MS: 556.0 [(M+Na)$^+$].

Anal. calc. for $C_{29}H_{27}NO_9 \cdot \frac{1}{4} H_2O$: C, 64.74; H, 5.15; N, 2.60. Found C, 64.76; H, 5.25; N, 2.50.

EXAMPLE 8

5-Carboxymethoxy-1-(2-carboxymethoxy-4-methoxybenzyl)-3-(3,4-methylenedioxyphenyl) indole-2-carboxylic acid a) Ethyl 5-carboethoxymethoxy-1-(2-carboethoxymethoxy-4-methoxybenzyl)-3-(3,4-methylenedioxyphenyl)indole-2-carboxylate. The title compound was prepared from ethyl 1-(2-carboethoxymethoxy-4-methoxybenzyl)-5-hydroxy-3-(3,4-methylenedioxyphenyl)indole-2-carboxylate (150 mg, 0.26 mmol) and ethyl bromoacetate (55 mg, 0.33 mmol) by the method given in example 7b (119 mg, 69%).

b) 5-Carboxymethoxy-1-(2-carboxymethoxy-4-methoxybenzyl)-3-(3,4-methylenedioxyphenyl)indole-2-carboxylic acid. The title compound was prepared from ethyl 5-carboethoxymethoxy-1-(2-carboethoxymethoxy-4-methoxybenzyl)-3-(3,4-methylenedioxyphenyl)indole-2-carboxylate (100 mg, 0.16 mmol) by the method given in example 3d (yield=76 mg, 87%); m.p. 203°–205° C.

MS: 572.0 [(M+Na)$^+$].

Anal. calc. for $C_{28}H_{23}NO_{11} \cdot \frac{1}{4} H_2O$: C, 60.71; H, 4.28; N, 2.53. Found C, 60.45; H, 4.14; N, 2.50.

EXAMPLE 9

1-(2-Carboxymethoxy-4-methoxybenzyl)-3-(3,4-methylenedioxyphenyl)indole-2-carboxylic acid a) Ethyl 3-bromoindole-1-(2-carboethoxymethoxy-4-methoxybenzyl)-2-carboxylate. Ethyl 3-bromoindole-2-carboxylate (900 mg, 3.33 mmol) was alkylated with 2-carboethoxymethoxy-4-methoxybenzyl chloride (1.11 g, 4.3 mmol) by the method given in example 1c to afford the title compound (0.97 g, 60%).

b) 1-(2-Carboxymethoxy-4-methoxybenzyl)-3-(3,4-methylenedioxyphenyl)indole-2-carboxylic acid. The title compound was prepared by the coupling of ethyl 3-bromoindole-1-(2-carboethoxymethoxy-4-methoxybenzyl)-2-carboxylate (500 mg, 0.93 mmol) with 4-(methylenedioxy)phenylboric acid 290 mg, 1.74 mmol) by the method given in example 5b followed by saponification using the method given in example 3d (277 mg, 63%); m.p. 195°–196° C.

MS: 493.3 [(M+NH$_4$)$^+$].

Anal. calc. for $C_{26}H_{21}NO_8 \cdot \frac{1}{4} H_2O$: C, 65.07; H, 4.51; N, 2.92. Found C, 64.86; H, 4.49; N, 2.87.

EXAMPLE 10

4-[1-[2-Carboxy-3-(3,4-methylenedioxyphenyl) indolyl]]-4-(4-methoxyphenyl)butyric acid a) Methyl 3-(4-methoxybenzoyl)propionate. To a solution of 3-(4-methoxybenzoyl)propionic acid (2.08 g, 10 mmol) in $CH_3CN$ (50 mL) stirred at ice bath temperature under an argon atmosphere was added 1,8-diazabicyclo[5.4.0]-undec-7-ene (1.9 mL, 12.5 mmol) followed by $CH_3I$ (1.25 mL, 20 mmol). The ice bath was removed and stirring continued for 5 h. The mixture was then partitioned between 3N HCl (50 mL) and EtOAc (75 mL). The organic extract was washed successively with $H_2O$, aqueous $NaHCO_3$, $H_2O$ and saturated aqueous NaCl and dried ($Na_2SO_4$). The solvent was removed in vacuo to afford the title compound (1.88 g, 85%) as a white solid.

b) Methyl 3-hydroxy-4-(4-methoxyphenyl)butyrate. To a stirred solution of methyl 3-(4-methoxybenzoyl)propionate (1.88 g, 8.5 mmol) in $CH_3OH$ (50 mL) at ice bath temperature under an argon atmosphere was added NaBH$_4$ (190 mg, 5 mmol). The reaction mixture was stirred 1 h at ice bath temperature then quenched by the cautious addition of EtOAc (100 mL) and 3N HCl (50 mL). The layers were separated and the aqueous layer was washed with EtOAc. The combined organic extract was washed successively with $H_2O$, aqueous $NaHCO_3$, $H_2O$ and saturated aqueous NaCl and dried ($Na_2SO_4$). The solvent was removed in vacuo to yield a white solid which was crystallized from Et$_2$O/hexanes to afford the title compound (1.59 g, 84%).

c) Methyl 3-chloro-4-(4-methoxyphenyl)butyrate. To a solution of methyl 3-hydroxy-4-(4-methoxyphenyl)butyrate (0.50 g, 2.32 mmol) with triethylamine (1.1 ml, 7.8 mmol) in $CH_2Cl_2$ (5 mL) stirred at ice bath temperature under an argon atmosphere was added methanesulfonyl chloride (0.26 mL, 3.4 mmol). After 30 min at ice bath temperature, the reaction mixture partitioned between 3N HCl (50 mL) and EtOAc (75 mL). The organic extract was washed successively with $H_2O$, aqueous $NaHCO_3$, $H_2O$ and saturated aqueous NaCl then dried ($Na_2SO_4$). The solvent was removed in vacuo to afford the title compound (453 mg, 84%) as an oil which crystallized on standing; m.p. 48°–49° C.

d) Methyl 4-[1-(3-bromo-2-carboethoxyindolyl)]-4-(4-methoxyphenyl)butyrate. To a solution of ethyl 3-bromoindole-2-carboxylate (469 mg, 1.75 mmol) in dry DMF stirred at ice bath temperature under an argon atmosphere was added NaH (66 mg of 80% oil dispersion, 2.19 mmol, oil removed by pentane wash) and stirring continued for 15 min. To this was added a solution of methyl 3-chloro-4-(4-methoxyphenyl)butyrate (453 mg, 1.87 mmol). The ice bath was removed and stirring continued for 17 h. The reaction mixture partitioned between 3N HCl (50 mL) and EtOAc (75 mL). The organic extract was washed successively with $H_2O$, aqueous $NaHCO_3$, $H_2O$ and saturated aqueous NaCl then dried ($Na_2SO_4$) and the solvent was removed in vacuo. purification by flash chromatography silica gel eluting with 35% $Et_2O$/hexanes) afforded the title compound (75 mg, 21%).

e) Methyl 4-[1-[2-carboethoxy-3-(3,4-methylenedioxyphenyl)indolyl]]-4-(4-methoxyphenyl) butyrate. A mixture consisting of methyl 4-[1-(3-bromo-2-carboethoxyindolyl)]-4-(4-methoxyphenyl)butyrate (70 mg, 0.15 mmol), tetrakis(triphenylphosphine)palladium(0) (10 mg 0.009 mmol), toluene (2 mL), 2M aqueous $Na_2CO_3$ (0.15 mL) and a solution of 3,4-(methylenedioxy) phenylboric acid (50 mg, 0.3 mmol) in $CH_3OH$ (1 mL) was stirred at 90° C. under an argon atmosphere for 17 h. The reaction mixture partitioned between 3N HCl (15 mL) and EtOAc (25 mL). The organic extract was washed successively with $H_2O$, aqueous $NaHCO_3$, $H_2O$ and saturated aqueous NaCl then dried ($Na_2SO_4$). The solvent was removed in vacuo to yield a dark oil (115 mg). Purification by flash chromatography (silica gel gradient elution from 25% $Et_2O$/hexanes to 50% $Et_2O$/hexanes) afforded the title compound (46 mg, 61%).

f) 4-[1-[2-Carboxy-3-(3,4-methylenedioxyphenyl) indolyl]]-4-(4-methoxyphenyl)butyric acid. To a warmed solution of methyl 4-[1-[2-carboethxy-3-(3,4-methylenedioxyphenyl)indolyl]]-4-(4-methoxyphenyl) butyrate (45 mg, 0.087 mmol) in EtOH (2 mL) was added 1N aqueous NaOH (2 mL). This solution was refluxed for 1.5 h then cooled to room temperature and diluted with $H_2O$ (10 mL). The mixture was concentrated under reduced pressure. The aqueous residue was extracted with $Et_2O$, and the $Et_2O$ extracts were discarded. The aqueous phase was acidified with 6N HCl and extracted several times with EtOAc. The combined EtOAc extracts were washed successively with $H_2O$ and saturated aqueous NaCl and dried ($Na_2SO_4$). The solvent was removed in vacuo to provide an oily residue which was crystallized from $Et_2O$ to afford the title compound (24 mg);. m.p. 204°–205° C.

MS: 474 [(M+H)$^+$].

EXAMPLES 11–19

The following examples were prepared by the methods given above.

1-(2-Chloro-4,5-methylenedioxybenzyl)-3-[2-(3-hydroxypropoxy]-4-methoxyphenyl)indole-2-carboxylic acid mp 177°–178° C.

1-(2-Chloro-4,5-methylenedioxybenzyl)-3-(2-hydroxymethyl-4-methoxyphenyl)indole-2-carboxylic acid mp 131°–132° C.

3-(2-Carboxy-4-methoxyphenyl)-1-(2-Chloro-4,5-methylenedioxybenzyl)indole-2-carboxylic acid mp 259°–261° C.

3-[2-(2-Carboxyethoxy)-4-methoxyphenyl]-1-(2-Chloro-4,5-methylenedioxybenzyl)indole-2-carboxylic acid mp 231°–233° C.

3-(2-Carboxymethyl-4-methoxyphenyl)-1-(2-Chloro-4,5-methylenedioxybenzyl)indole-2-carboxylic acid mp 237°–239° C.

3-[2-[(E)-2-Carboxyethenyl]-4-methoxyphenyl]-1-(2-Chloro-4,5-methylenedioxybenzyl)indole-2-carboxylic acid mp 285°–287° C.

3-[2-(2-Carboxyethyl)-4-methoxyphenyl]-1-(2-Chloro-4,5-methylenedioxybenzyl)indole-2-carboxylic acid mp 229°–230° C.

1-(4-Carboxynaphth-1-ylmethyl)-3-(3,4-methylenedioxyphenyl)indole-2-carboxylic acid mp 130° C.

1-(2'-Carboxybiphen-4-ylmethyl)-3-(3,4-methylenedioxyphenyl)indole-2-carboxylic acid mp 147° C.

EXAMPLE 20

Formulations for pharmaceutical use incorporating compounds of the present invention can be prepared in various forms and with numerous excipients. Examples of such formulations are given below.

Inhalant Formulation

A compound of formula I, (1 mg to 100 mg) is aerosolized from a metered dose inhaler to deliver the desired amount of drug per use.

| Tablets/Ingredients | Per Tablet |
|---|---|
| 1. Active ingredient (Cpd of Form. 1) | 40 mg |
| 2. Corn Starch | 20 mg |
| 3. Alginic acid | 20 mg |
| 4. Sodium alginate | 20 mg |
| 5. Mg stearate | 1.3 mg |
| | 2.3 mg |

| Procedure for tablets: | |
|---|---|
| Step 1 | Blend ingredients No. 1, No. 2, No. 3 and No. 4 in a suitable mixer/blender. |
| Step 2 | Add sufficient water portion-wise to the blend from Step 1 with careful mixing after each addition. Such additions of water and mixing until the mass is of a consistency to permit its converion to wet granules. |
| Step 3 | The wet mass is converted to granules by passing it through an oscillating granulator using a No. 8 mesh (2.38 mm) screen. |
| Step 4 | The wet granules are then dried in an oven at 140° F. (60° C.) until dry. |
| Step 5 | The dry granules are lubricated with ingredient No. 5. |
| Step 6 | The lubricated granules are compressed on a suitable tablet press. |

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of the formula (I)

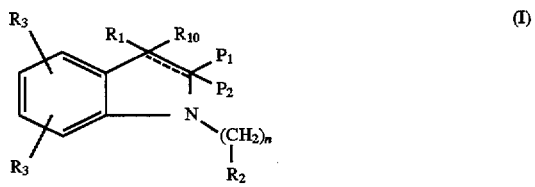

wherein:

$R_1$ is —$X(CH_2)_n Ar$ or —$X(CH_2)_n R_8$ or

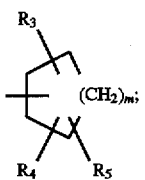  (c)

$R_2$ is Ar or (c);

$P_1$ is —$X(CH_2)_n R_8$;

$P_2$ is —$X(CH_2)_n R_8$, or —$XR_9 Y$;

$R_3$ and $R_5$ are independently hydrogen, $R_{11}$, OH, $C_{1-8}$alkoxy, $S(O)_q R_{11}$, $N(R_6)_2$, Br, F, I, Cl, $CF_3$, $NHCOR_6$, —$R_{11}CO_2R_7$, —$XR_9$—Y, XY or —$X(CH_2)_n R_8$ wherein the methylene groups of —$X(CH_2)_n R_8$ may be unsubstituted or substituted by one or more —$(CH_2)_n Ar$ groups;

$R_4$ is hydrogen, Ar, $R_{11}$, OH, $C_{1-5}$alkoxy, $S(O)_q R_{11}$, $N(R_6)_2$, —$X(R_{11})$, Br, F, I, Cl or $NHCOR_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen, $C_{1-6}$alkyl or $(CH_2)_n Ar$;

$R_8$ is hydrogen, $R_{11}$, $CO_2R_7$, $CO_2C(R_7)_2 O(CO)XR_7$, —$N(R_7)SO_2R_7$, $PO_3(R_7)_2$; $SO_2NR_7R_{11}$, $CONR_7SO_2R_{11}$, $SO_3R_7SO_2R_7$, $SO_3R_7$, $SO_2R_7$, $P(O)(OR_7)R_7$, CN —$C(O)N(R_6)_2$, tetrazole or $OR_6$;

$R_9$ is monovalent or divalent $C_{1-10}$alkyl, $C_{2-10}$alkenyl or phenyl all of which may be unsubstituted or substituted by one or more OH, $N(R_6)_2$, COOH, halogen or $XC_{1-5}$alkyl;

$R_{10}$ is $R_3$ or $R_4$;

$R_{11}$ is monovalent or divalent $C_{1-8}$alkyl, $C_{2-8}$alkenyl, $C_{2-8}$alkynyl all of which may be unsubstituted or substituted by one or more OH, $CH_2OH$, $N(R_6)_2$ or halogen;

X is $(CH_2)_n$, O, $NR_6$ or $S(O)_q$;

Y is $CH_3$ or $X(CH_2)_n Ar$;

Ar is:

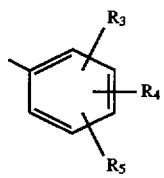  (a)

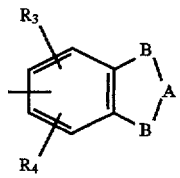  (b)

naphthyl, indolyl, pyridyl, thienyl, oxazolidinyl, oxazolyl, thiazolyl, is othiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or $(C(R_6)_2)_m$;

B is —$CH_2$— or —O—;

q is zero, one or two;

n is an integer from 0 to six;

m is 1, 2 or 3;

and the dotted line indicates the optional presence of a double bond; or a pharmaceutically acceptable salt thereof; provided that when the optional double bond is present there is no $P_1$ or $R_{10}$; and further provided that X is not oxygen for $R_1$.

2. A compound of claim 1 wherein $R_1$ is $X(CH_2)_n Ar$, dihydrobenzofuranyl, benzodioxanyl, cyclohexyl, or $C_{1-4}$alkyl and Ar is (a), (b) or pyridyl; $R_2$ is (a), (b) or indolyl; $R_3$ and $R_5$ are independently hydrogen, OH, $C_{1-5}$alkoxy, Br, Cl, I, F, —$OC_{1-4}$alkyl phenyl, $R_{11}CO_2R_7$, $C_{1-4}$alkyl, $N(R_6)_2$, $NH(CO)CH_3$, —$X(CH_2)_n R_8$, phenyl or $S(O)_p C_{1-5}$alkyl; $R_4$ is hydrogen, OH, $C_{1-5}$alkoxy, halogen, $C_{1-4}$alkyl, $N(R_6)_2$, $NH(CO)CH_3$ or $S(O)_p C_{1-5}$alkyl; $P_1$ and $P_2$ are independently hydrogen, $CO_2H$ or tetrazole; and X is $(CH_2)_n$ or oxygen.

3. A compound of claim 2 wherein $R_3$ is hydrogen or —$X(CH_2)_n R_8$, $R_{11}CO_2R_7$; $R_4$ and $R_5$ are independently hydrogen, OH, $C_{1-5}$alkoxy, $SC_{1-5}$alkyl, F, Br, $C_{1-3}$alkyl or $NH_2$.

4. A compound of claim 3 wherein $R_1$ is (b) and $R_2$ is (a) or (b); A is $CH_2$, B is —O—; there is an optional double bond; $R_3$ is hydrogen, $X(CH_2)_q COOH$ or $CH=CHCO_2H$, $R_4$ is hydrogen, or $C_{1-2}$alkoxy; and $R_5$, $R_{10}$ and $P_2$ are hydrogen.

5. A compound of claim 1 selected from the group consisting of:

1-(3,4-Methylenedioxybenzyl)-3-(4-methoxyphenyl) indole-2-carboxylic acid;

1-(2-Chloro-4,5-methylenedioxybenzyl)-3-(4-methoxyphenyl)indole-2-carboxylic acid;

3-(3,4-Methylenedioxyphenyl)-1-(4-methoxybenzyl) indole-2-carboxylic acid;

3-(2-Carboxymethoxy-4-methoxyphenyl)-1-(2-chloro-4,5-methylenedioxybenzyl)indole-2-carboxylic acid;

5-Benzyloxy-1-(2-carboxymethoxy-4-methoxybenzyl)-3-(3,4-methylenedioxyphenyl)indole-2-carboxylic acid;

1-(2-Carboxymethoxy-4-methoxybenzyl)-5-hydroxy-3-(3,4-methylenedioxyphenyl)indole-2-carboxylic acid;

1-(2-Carboxymethoxy-4-methoxybenzyl)-3-(3,4-methylenedioxyphenyl)-5-(prop-1-yloxy)indole-2-carboxylic acid;

5-Carboxymethoxy-1-(2-carboxymethoxy-4-methoxybenzyl)-3-(3,4-methylenedioxyphenyl)indole-2-carboxylic acid;

1-(2-Carboxymethoxy-4-methoxybenzyl)-3-(3,4-methylenedioxyphenyl)indole-2-carboxylic acid;

4-[1-[2-Carboxy-3-(3,4-methylenedioxyphenyl)indolyl]]-4-(4-methoxyphenyl)butyric acid.

6. A pharmaceutical composition comprising a sufficient amount of a compound of claim 1 and a pharmaceutically acceptable carrier.

7. A method of antagonizing endothelin receptors which comprises administering to a subject in need thereof, an effective amount to antagonize endothelin receptors of a compound of claim 1.

8. A method of treating hypertension which comprises administering to a subject in need thereof an effective amount of a compound of claim 1.

9. A method of treating renal failure which comprises administering to a subject in need thereof, an effective amount of a compound of claim 1.

10. A method of treating cerebrovascular disease which comprises administering to a subject in need thereof, an effective amount of a compound of claim 1.

* * * * *